United States Patent

Liu et al.

[11] Patent Number: 6,080,393
[45] Date of Patent: *Jun. 27, 2000

[54] SKIN CARE COMPOSITION COMPRISING A RETINOID

[75] Inventors: Jue-Chen Liu, Neshanic; Jonas C. T. Wang, Robbinsville; Mohammed Yusuf, Edison, all of N.J.; Norihiro Yamamoto, Koriyama; Satoshi Kazama, Sukagawa, both of Japan

[73] Assignee: Johnson & Johnson Consumer Products, Inc., Skillman, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/523,836

[22] Filed: Sep. 6, 1995

[30] Foreign Application Priority Data

Jul. 9, 1994 [JP] Japan .................................. 6-238639

[51] Int. Cl.$^7$ ........................................ A61K 9/107
[52] U.S. Cl. ..................... 424/78.03; 424/401; 424/450; 514/938; 514/946
[58] Field of Search ................... 424/45, 401, 450, 424/78.03; 514/938, 946

[56] References Cited

U.S. PATENT DOCUMENTS

| 4,826,828 | 5/1989 | Wilmott et al. ............................ 514/63 |
| 4,877,805 | 10/1989 | Kligman .................................. 514/381 |

FOREIGN PATENT DOCUMENTS

| 94/01074 | 1/1994 | WIPO . |
| 95/2226709 | 10/1995 | WIPO . |

*Primary Examiner*—Raj Bawa

[57] ABSTRACT

A skin care composition comprising an oil-in-water emulsion and a therapeutically effective amount of a retinoid selected from the group consisting of Vitamin A alcohol, Vitamin A aldehyde, retinyl acetate, retinyl palmitate and mixtures thereof, the composition having a pH of between about 4 and about 10 and further comprising an oil phase comprising one or more oils having a total unsaturation density, or C value, of about 1200 or less.

19 Claims, 5 Drawing Sheets

SKIN CARE COMPOSITION COMPRISING A RETINOID

This application hereby incorporates by reference Japanese Patent Application No. Hei 6-238639, filed Sep. 7, 1994 and from which this application claims the benefit of priority.

FIELD OF THE INVENTION

This invention relates to skin care compositions containing retinoids which generally improve the quality of the skin, particularly human facial skin. More particularly, the present invention relates to chemically stable skin care compositions comprising an oil-in-water emulsion and certain retinoids and to methods for making such compositions.

BACKGROUND OF THE INVENTION

Skin care compositions containing retinoids have become the focus of great interest in recent years. Retinoic acid, also known as Vitamin A acid or tretinoin, is well-known for the treatment of such skin conditions as acne and products containing retinoic acid are commercially available in various forms from the Dermatological Division of Ortho Pharmaceutical Corporation. Such products, for example, include Retin A* creams, an oil-in-water emulsion of retinoic acid containing as an oil-soluble antioxidant, butylated hydroxytoluene (BHT); Retin A* liquid, a solution of retinoic acid in a polyethylene glycol/ethanol solvent employing BHT as an antioxidant; and Retin A* gel, which comprises retinoic acid in a gel vehicle comprising ethyl alcohol as the solvent, hydroxypropyl cellulose as the thickener or gelling agent and BHT as an antioxidant. These retinoic acid containing products have proven stable and capable of providing active ingredients after extended periods of storage.

More recently, however, wider use of retinoids has been suggested for treatments other than acne such as, for example, the treatment of skin against photoaging and sun damage. Many individuals who have had a good deal of sun exposure in childhood will show the following gross cutaneous alterations in later adult life: wrinkling, leatheriness, yellowing, looseness, roughness, dryness, mottling (hyperpigmentation) and various premalignant growths (often subclinical). These changes are most prominent in light-skinned persons who burn easily and tan poorly. These cumulative effects of sunlight are often referred to as "photoaging". Although the anatomical degradation of the skin is most advanced in the elderly, the destructive effects of excessive sun exposure are already evident by the second decade. Serious microscopic alterations of the epidermis and dermis occur decades before these become clinically visible. Wrinkling, yellowing, leatheriness and loss of elasticity are very late changes.

The problem of skin aging is addressed in U.S. Pat. No. 4,603,146, wherein Vitamin A acid in an emollient vehicle is suggested as a treatment. Further, in U.S. Pat. No. 4,877,805, it is suggested that a number of retinoids are useful for restoring and reversing sun damage of human skin.

When considering the use of retinoids in skin care products, it is believed that certain retinoids such as, for example, retinol (Vitamin A alcohol), retinal (Vitamin A aldehyde) and retinyl esters such as retinyl acetate and retinyl palmitate would be preferred over retinoic acid. This is because they are endogenous compounds naturally occurring in the human body and essential for good growth, differentiation of the epithelial tissues and reproduction. Additionally, excess retinol is stored in the human body largely in an inactive ester form, e.g., retinyl palmitate and, to some extent, retinyl acetate. The aldehyde, retinal, also a preferred form, is an active metabolite of retinol. Accordingly, attention has turned toward formulating skin care compositions which contain these preferred, naturally occurring retinoids.

In formulating products containing such retinoids, the same properties sought with respect to the retinoic acid formulas are desirable for other retinoid containing compositions. Specifically, much attention is directed toward providing a composition which is aesthetically pleasing and which can deliver active ingredients after a substantial shelf life. Not surprising, in formulating products containing such retinoids, the art is led to the experience gained in the already existing formulas containing retinoic acid. Typically, such formulas comprise oil-in-water emulsions wherein the retinoic acid is carried within the oil phase and is protected from oxidation by employing an oil-soluble antioxidant. With respect to the form of the emulsion, oil-in-water emulsions have been preferred in that, as compared to water-in-oil emulsions for example, they are non-occlusive, non-greasy, compatible with other such emulsion products, easy to remove from the skin and are regarded as more aesthetically pleasing as well as being more economical to manufacture. With respect to chemical stability of the active ingredient, it has been experienced that the retinoic acid in the oil phase is, in the main, well protected by including in such oil phase an oil soluble antioxidant. Thus, various oil-in-water emulsions containing retinoic acid and BHT, as oil-soluble antioxidant have been described and sold, for example, in U.S. Pat. No. 3,906,108, U.S. Pat. No. 4,66,805, and U.S. Pat. No. 4,247,547. The retinoic acid containing compositions described in these patents have proven to be, or are said to be, chemically stable. Therefore, a number of skin care products have appeared in the marketplace incorporating other retinoids, including, for example, retinol, retinal and retinyl esters such as retinyl acetate and retinyl palmitate, and these unsurprisingly emulate the formulas of the commercial retinoic acid compositions, i.e., are oil-in-water emulsions protected by oil-soluble antioxidants. Unfortunately, it has been found that these other retinoids in such compositions quickly lose their activity and either oxidize or isomerize to non-efficacious chemical forms with the result that the amount of retinoid actually available to provide the beneficial effects of the product is reduced, in an unacceptably short period of time, to an ineffective quantity and eventually to only trace quantities.

There have been attempts to formulate a stable composition comprising retinol, retinal, retinyl acetate and retinyl palmitate in oil-in-water emulsions, such as in U.S. Pat. No. 4,826,828. Avon Products, Inc., the assignee of U.S. Pat. No. 4,826,828, sells two skin care products called Bioadvance and Bioadvance 2000. Each of these products is supplied in two bottles, portions of which are mixed together just prior to use. U.S. Pat. No. 4,720,353 (Bell) describes water-in-oil emulsion carriers for various medicaments and drugs intended for topical application to the skin. Other water-in-oil type emulsions have been described in EP 0 343 444 A2 (Siemer et al.) and EP 0 330 496 A2 (Batt).

Clum et al., in U.S. patent application Ser. No. 07/719, 264, now abandoned, describe stable water-in-oil compositions containing a retinoid and a stabilizing system selected form the group consisting of: (a) a chelating agent and at least one oil-soluble antioxidant; (b) a chelating agent and at least one water-soluble antioxidant; and an antioxidant present in each of the oil and water phases of the emulsion.

This composition retains at least about 60% of the retinoids after 13 weeks of storage at 40° C. Although this system is quite stable and useful in retinoid-containing products, it is nevertheless a water-in-oil emulsion and retains all the attributes, advantages and disadvantages of such a formulation. It is therefore an object of this invention to provide an oil-in-water formulation which is stable and acceptable for use on the skin.

SUMMARY OF THE INVENTION

In accordance with the present invention, it has now been unexpectedly found that certain retinoids may be successfully stabilized against chemical degradation by incorporating them into oil-in-water emulsions comprising a specifically defined stabilizing system.

The retinoids which can be stabilized against chemical degradation in accordance with the principles of the present invention are retinol (Vitamin A alcohol), retinal (Vitamin A aldehyde), retinyl acetate, retinyl palmitate and mixtures thereof. It is also theorized that other retinoids, including synthetic retinoids and retinoid-like chemicals may benefit from inclusion in the formulations of this invention.

As used herein, the "chemical stability" or "stability" of a retinoid is defined in terms of the percentage of the specified retinoid which is retained in its original chemical form after the composition has been stored for a specified period of time at a specified temperature. Thus, if the original concentration of all-trans retinol in an absolute ethanol solution were 0.20% by weight and, after two (2) weeks' storage at room temperature (21° C.+1° C.), the concentration of all-trans retinol were 0.18% by weight, then the original solution would be characterized as having a chemical stability of 90% after two weeks' storage at room temperature. In the same fashion, if an emulsion comprising all-trans retinol had an initial concentration of 0.30% by weight and after storage for 13 weeks at 40° C. had a concentration of all trans-retinol of 0.24% by weight, then the original emulsion retinol of 80% after 13 weeks' storage at 40° C.

Specifically, a commercially usable composition should exhibit a stability of at least about 60% of the active retinoid(s) after 13 weeks storage at 40 C. Preferably, the compositions of this invention exhibit a stability of at least about 70% after 13 weeks' storage at 40 C.

Accordingly, there is provided, in accordance with the teachings of this invention, a skin care composition comprising an oil-in-water emulsion and a retinoid selected from the group consisting of retinol, retinal, retinyl acetate, retinyl palmitate and mixtures thereof, said composition having a pH of between about 4 and about 10; said composition further comprising an oil phase, said oil phase having a relatively low level of unsaturation; said composition further comprising a which acts to render stable the retinoid in the skin care composition of this invention, said stabilizing system being selected from the group consisting of:

a) at least one oil-soluble antioxidant;
 b) a chelating agent and at least one oil-soluble antioxidant;
 c) a chelating agent; and
 d) a chelating agent and an antioxidant present in each of the oil and water phases of said emulsion; said composition retaining at least about 70% of said retinoids after 13 weeks' storage at 40° C. It is theorized that including a predominantly saturated oil and appropriate pH, a stabilizing system may not be necessary.

DETAILED DESCRIPTION OF THE PREFERRED EMBODIMENTS

As described above, the composition of the invention is in the form of a particular type of emulsion, namely oil-in-water. As used herein, the generally accepted concept of an emulsion applies, i.e., an intimate mixture of two immiscible liquids which remains unseparated for an acceptable shelf life at or about room temperature. Ordinarily, when two immiscible liquids are mechanically agitated, both phases initially tend to form droplets. Thereafter, when the agitation ceases, the droplets quickly coalesce, and the two liquids tend to separate. On the other hand, an emulsion may be formed and physically stabilized and the lifetime of the droplets in intimate mixture materially increased if a compound, referred to as an emulsifier, is added to the immiscible liquids. Usually only one phase persists in droplet form for a prolonged period of time, and this is referred to as the internal phase which is surrounded by an external phase. An oil-in-water emulsion is one in which the external phase (also called the continuous phase) comprises water or an aqueous solution and the internal phase (also called the discontinuous or disperse phase) comprises an oil or mixture of mutually soluble oils.

The present invention has overcome these difficulties and provides oil-in-water emulsion compositions containing at least one retinoid compound wherein the physical stability of the emulsion and the chemical stability of the active ingredients is excellent. The present invention also provides a method for making such emulsion compositions and a method and apparatus for storing such emulsion compositions in order to maintain their stability during storage and prior to use by the consumer.

The skin care compositions of the present invention comprising an oil-in-water emulsion can be in the format of cream or lotion formulations, as desired, by varying the relative quantities of the oil and water phases of the emulsion. The pH of the compositions should be in the range of from about 4 to about 10; preferably they should be from about 6 to about 8. It has been found that, in compositions having a pH of about 6 or more, the retinoid is more stable than at pH of less than 6. Furthermore, the stability of the retinol is less dependent upon the actual materials used in the formulation at pH of 6 or more.

Preferably, the oils used in the compositions of this invention are relatively highly saturated, preferably those having a relatively low iodine value. The contribution to unsaturation, density C, of an individual oil in the composition is calculated as follows:

$$C = A \times B,$$

where A is the percentage of the unsaturated oil or fat used in an oil-in-water emulsion and B is the iodine value of the unsaturated oil. If a mixture of oils is used in the oil phase, the total unsaturation density will be the sum of all individual C values. Accordingly, an oil phase having an unsaturation density or total C of 1200 or less and preferably 500 or less should be used in the formulations of this invention. It is theorized that saturated oils and/or fats are less reactive than unsaturated oils and fats, due to the presence of reactive double bonds in unsaturated oils and fats, which can initiate reactions with the retinoids and other materials in the compositions of this invention. Synthetic oils that are useful are fatty acid esters, fatty alcohols, for example, octyl hydroxystearate, cetyl palmitate, cetyl alcohol, glyceryl stearate and PEG-100 stearate, stearyl alcohol, octyl pelargonate and the like. Examples of preferred oils are as follows: Finsolv (available from Finetex of New Jersey), Miglyol A12 (available from Huls Corporation of New York), silicone oil (Dow Corning of Minnesota), mineral oil, and the like, having very low iodine values are also quite useful in the compositions of this invention. Furthermore, the percentage of the oil present in the compositions of this invention is also relevant: the lower the percentage of high-iodine value oil, the more stable the retinoid in the composition.

It is also preferable to have at least one oil-soluble antioxidant in the compositions of this invention. The oil-soluble antioxidants which are useful in the compositions of the present invention include butylated hydroxytoluene (BHT), ascorbyl palmitate, butylated hydroxanisole (BHA), phenyl-α-naphthylamine, hydroquinone, propyl gallate, nor-dihydroguiaretic acid, and mixtures thereof as well as any other known oil-soluble antioxidant compatible with the other components of the compositions.

Preferably, a water-soluble antioxidant should be present in the water phase of the compositions of this invention. The water-soluble antioxidants which are useful in the compositions of this invention include ascorbic acid, sodium metabisulfite, sodium bisulfite, sodium thiosulfite, sodium formaldehyde sulfoxylate, isoascorbic acid, thioglyerol, thiosorbitol, thiourea, thioglycolic acid, cysteine hydrochloride, 1,4-diazobicyclo-(2,2,2)-octane and mixtures thereof as well as any other known water-soluble antioxidant compatible with the other components of the compositions.

The composition of this invention can contain additives, as required, such as a humectant, an antioxidant, a preservative, a flavor, a surface active agent, a binder, and the like.

Examples of the humectant include glycerol, sorbitol, propylene glycol, ethylene glycol, 1,3-butylene glycol, polypropylene glycol, xylitol, malitol, lactitol and the like. They may be used either singly or in combination.

Examples of the preservatives include salicylic acid, chlorhexidine hydrochloride, phenoxyethanol, sodium benzoate, methyl para-hydroxybenzoate, ethyl para-hydroxybenzoate, propyl para-hydroxybenzoate, butyl para-hydroxybenzoate and the like.

Examples of the flavor include menthol, anethole, carvone, eugenol, limonene, ocimene, n-decylalcohol, citronellol, a-terpineol, methyl salicylate, methyl acetate, citronellyl acetate, cineole, linalool, ethyl linalool, vanillin, thymol, spearmint oil, peppermint oil, lemon oil, orange oil, sage oil, rosemary oil, cinnamon oil, pimento oil, cinnamon leaf oil, perilla oil, wintergreen oil, clove oil, eucalyptus oil and the like.

Examples of surface active agents include surface sodium alkyl sulfates, e.g., sodium lauryl sulfate and sodium myristyl sulfate, sodium N-acyl sarcosinates, e.g., sodium N-lauroyl sarcosinate and sodium N-myristoyl sarcosinate, sodium dodecylbenzenesulfonate, sodium hydrogenated coconut fatty acid monoglyceride sulfate, sodium lauryl sulfoacetate and N-acyl glutamates, e.g., N-palmitoyl glutamate, N-methylacyltaurin sodium salt, N-methylacylalanine sodium salt, sodium a-olefin sulfonate and sodium dioctylsulfosuccinate; N-alkylaminoglycerols, e.g., N-lauryldiaminoethylglycerol and N-myristyldiaminoethylglycerol, N-alkyl-N-carboxymethylammonium betaine and sodium 2-alkyl-1-hydroxyethylimidazoline betaine; polyoxyethylenealkyl ether, polyoxyethylenealkylaryl ether, polyoxyethylenelanolin alcohol, polyoxyethyleneglyceryl monoaliphatic acid ester, polyoxyethylenesorbitol aliphatic acid ester, polyoxyethylene aliphatic acid ester, higher aliphatic acid glycerol ester, sorbitan aliphatic acid ester, Pluronic type surface active agent, and polyoxyethylenesorbitan aliphatic acid esters such as polyoxyethylenesorbitan monooleate and polyoxyethylenesorbitan monolaurate.

Examples of the binder or thickener include cellulose derivatives such as alkali metal salts of carboxymethylcellulose, methyl cellulose, hydroxyethyl cellulose and sodium carboxymethylhydroxyethyl cellulose, alkali metal alginates such as sodium alginate, propylene glycol alginate, gums such as carrageenan, xanthan gum, tragacanth gum, caraya gum and gum arabic, and synthetic binders such as polyvinyl alcohol, polysodium acrylate and polyvinyl pyrrolidone.

Thickeners such as natural gums and synthetic polymers, as well as preservatives such as methylparaben, butyl paraben, propylparaben and phenoxyethanol, coloring agents and fragrances also are commonly included in such compositions.

The antioxidants should be utilized in a stabilizing effective amount and may range in total from about 0.001 to 5% based on the weight of the total composition, preferably from about 0.01 to about it. The amount of antioxidants utilized in the compositions of the present invention is dependent in part on the specific antioxidants selected, the amount of and specific retinoid being protected and the processing conditions.

In certain aspects of this invention, the compositions should include a chelating agent. The retinoid compounds of this invention are sensitive to metal ions and in particular to bi- and tri-valent cations and in certain instances, appear to degrade rapidly in this presence. The chelating agent forms a complex with the metal ions thereby inactivating them and preventing them from affecting the retinoid compounds. Chelating agents which are useful in the compositions of the present invention include ethylenediamine tetra acetic acid (EDTA) and derivatives and salts thereof, dihydroxyethyl glycine, citric acid, tartaric acid, and mixtures thereof. The chelating agents should be utilized in a stabilizing effective amount and may range from about 0.01 to about 2% based on the weight of the total composition, preferably from about 0.05 to about 1%. Most preferably, the chelating agent should be EDTA.

The retinoid compounds which are useful in the compositions of the present invention consist of Vitamin A alcohol (retinol), Vitamin A aldehyde (retinal) and Vitamin A esters (retinyl acetate and retinyl palmitate). These retinoids are utilized in the compositions of the present invention in a therapeutically effective amount that may range from about 0.001 to about 5% by weight of the total compositions, preferably from about 0.001 to about 1%.

In addition to such oils, other emollients and surface active agents have been incorporated in the emulsions, including glycerol trioleate , acetylated sucrose distearate, sorbitan trioleate, polyoxyethylene (1) monostearate, glycerol monooleate, sucrose distearate, polyethylene glycol (50) monostearate, octylphenoxypoly (ethyleneoxy) ethanol, decaglycerin penta-isostearate, sorbitan sesquioleate, hydroxylated lanolin, lanolin, triglyceryl diisostearate, polyoxyethylene (2) oleyl ether, calcium stearoyl-2-lactylate, methyl glucoside sesquistearate, sorbitan monopalmitate, methoxy polyethylene glycol-22/dodecyl glycol copolymer (Elfacos E200), polyethylene glycol-45/dodecyl glycol copolymer (Elfacos ST9), polyethylene glycol 400 distearate, and lanolin derived sterol extracts, glycol stearate and glycerol stearate; alcohols, such as cetyl alcohol and lanolin alcohol; myristates, such as isopropyl myristate; cetyl palmitate; cholesterol; stearic acid; propylene glycol; glycerine, sorbitol and the like.

Other active ingredients such as sunscreen materials and antimicrobial materials may be utilized in the compositions of the present invention provided that they are physically and chemically compatible with the other components of the compositions. For example, moisturizing agents such as propylene glycol, allantoin, acetamine MEA, oat protein and hyaluronic acid and other humectants may be added to the retinoid-containing formulations of this invention in order to provide moisturizing activity in conjunction with the retinoid-related activity of the products. Sunscreens may include organic or inorganic sunscreens, such as methoxyoctylcinnamate and other cinnamate compounds, titanium dioxide and zinc oxide and the like.

Various irritancy mitigants may be added to the compositions of this invention. Retinoid-containing compositions tend to irritate the skin, therefore irritancy mitigants assist in preventing undue discomfort to the user, while potentially permitting the dosage level of retinoid to be increased, thereby making the product more effective. Irritancy mitigants such as α-bisabolol, panthenol, allantoin, ginkgo biloba, stearoyl glycerrhetinic acid (licorice extract), tea tree oil, butchers' broom, calendula, ginseng and the like may be added.

Other ingredients may include agents which assist in protecting the skin from aging, such as sunscreens, antioxidant vitamins such as ascorbic acid, vitamin B, biotin, pantothenic acid, vitamin D, vitamin E and vitamin C, and sodium bisulfite. Yeast extract, gingko biloba, bisabolol, panthenol, alpha hydroxy acids and oligosaccharides such as melibiose are among other ingredients which assist in preventing aging of the skin by such means as irritation mitigation, oxidation mitigation, healing, affecting retinoid metabolism and inhibiting the production of elastase.

Skin color evening ingredients may also be effective in the products of this invention. Such ingredients may include hydroquinone, licorice extract, kojic acid, gatuline A (pilewort extract), micromerol (butylene glycol and apple extract) and like depigmentation agents.

Compositions which assist in the reduction of lines and wrinkles may also be added to the compositions of this invention. For example, alpha hydroxy acids, hyaluronic acid, Gatuline R (fagus silvitica extract), pigments and scattering aids such as zinc oxide and titanium dioxide may be used in the compositions of this invention in this capacity.

Anti-inflammatory agents may also be used in the compositions of this invention. Not only should these agents assist in mitigating irritation, they may assist the retinoids in treating wrinkles and lines in the skin. Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxycorticosterone acetate, dexamethoasone, dichlorisone, deflorasonediacetate, diflucortolone valerate, fluadronolone, fluclarolone acetonide, fludrocortisone, flumethasone pivalate, fluosinolone acetonide, fluocionide, flucortine butylester, fluocortolone, flupredidene (flupredylidene) acetate, flurandronolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone and its esters, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone and mixtures thereof may be used. Preferably, hydrocortisone may be used.

Nonsteroidal anti-inflammatory agents may also be employed in the compositions of this invention, such as salicylates, acetic acid derivatives, fenamates, propionic acid derivatives and pyrazoles or mixtures thereof. Other synthetic and natural anti-inflammatory agents may also be used.

Additional active ingredients having topical activity may be utilized in the compositions of this invention. Azole-type anti-fungal and anti-bacterial agents may be employed in the compositions of this invention in their base form. For example, ketoconazole, miconazole, itraconazole, elubiol, and like related imidazole antifungals and antibacterials are useful in the topical formulations of this invention.

The compositions of the present invention can be prepared by well-known mixing or blending procedures. Each phase of the emulsion is preferably separately prepared with all of the components contained in the appropriate phase, except that it is usually preferred to omit the retinoid compound initially. The emulsion is then formed normally by adding the oil phase to the water phase with agitation, and the emulsion should be cooled down when the retinoid compound is added. It is preferred that the portions be prepared under oxygen-depleted atmosphere such as a nitrogen or argon gas blanket. Most preferably, argon or nitrogen gas is bubbled through the water phase prior to phasing in the oil phase. Commercially, it is envisioned that such oxygen depleted atmosphere may be obtained by operating under vacuum conditions and that the product be stored, prior to use, in blind-end containers, preferably aluminum tubes.

This invention relates not only to stable retinoid-containing compositions used in skin care, and to methods of making such compositions, it also relates to an apparatus and method of storing such compositions prior to use.

It has been found that by using a pouch-type container in which a composition is out of contact with oxygen, the composition can be used as not only a water-in-oil type emulsion but also an oil-in-water type emulsion. Further, even after use is begun, the contact with oxygen can be blocked, making it possible to substantially prevent decomposition or degradation of the retinoid in the skin care composition.

More specifically, this invention relates to a container in which the skin care composition is out of contact with oxygen in a two-compartment container such as a pouch-type container, further to a skin care composition which is stored in a two-compartment container which are made of films. Preferably, the film materials of the inner container are formed from a monolayer film or multilayer film. The film materials are preferably selected from the following materials: aliumin and AAS and ethylene-vinyl alcohol compolymer. More preferably, the pouch-type container contains film materials which are laminated in the following order, beginning from the innermost portion of the film: polyethylene terephthalate, nylon, aluminum and an AAS resin or polypropylene. Further, this inveniton relates to a skin care composition which is stored in a container having an aerosol-system using a liquefied gas or a compressed gas.

The skin care composition should neither be directly contacted with oxygen or an oxygen-containing gas such as air, nor contacted with oxygen passing through the wall of the container. Portions in contact with the outside, which constitute the container, such as a wall, an opening, etc. of the container, are required to have excellent oxygen barrier properties. The container must also be designed not to pass oxygen when feeding the skin care composition to the container or when removing the composition from the container.

If such a requirement is satisfied, the shape of the container in which the composition is out of contact with oxygen is not particularly limited in this invention, and can be a tube, a pump dispenser, a compressed dispenser, a bottle, a spray, a sachet or the like. From the aspects of production, treatment and an oxygen-barrier type, the two-compartment container is preferred and, the pouch-type container is especially preferred. Such a two-compartment container generally means a container consisting of an outer container and an inner container which is accommodated in the outer container and stores the content therein, but is not particularly restricted if the container can store and isolate the content from outside. A "pouch-type container" means a container having an outer container and a pouch which is accommodated in the outer container, is provided with a valve which stores the contents therein.

This pouch is a bag-like container whose wall is formed of a film and which is provided with an opening through which to pass the contents. The two-part container actually used is preferably an aerosol-system. The aerosol-system here referred to is a system in which the inside of the container is kept in a state pressurized with a propellant, and the content is sprayed with the propellant by opening a valve, or a system in which the content is discharged outside the container with the pressure of the propellant.

A liquefied gas or a compressed gas is used as a propellant. Examples of the liquefied gas include chlorofluorocarbons, dimethyl ether, liquefied petroleum gas (LPG) and chlorinated hydrocarbons. Examples of the compressed gas include a nitrogen gas, a carbon dioxide gas, a nitrous oxide ($N_2O$) and argon. The liquefied gasses are preferable when considering a uniformity of discharge amount of the content, and the compressed gasses are preferable judging from interaction with the content, influence on the human body and the like.

An ordinary aerosol is generally formed by charging a stock solution and propellant in a container and sealing the container with a valve. In a general filling method, the content is charged into the container from an opening, and after the opening is sealed with a valve the propellant is further charged. According to such an ordinary filling method, however, it is quite difficult to prevent the contact between the content such as a lotion or the like and oxygen. There is further a problem that the content is directly contacted with the propellant within the pouch by being partially mixed therewith. Taking into account the problem of stability of the retinoid compound, the container of the ordinary aerosol-system in which the content is mixed with the propellant cannot be used in the skin care composition of this invention.

Accordingly, the two-part container in this invention, unlike the ordinary container, consists of an outer container and a pouch having a valve. Only the content (skin care composition) is contained in the inner container and the propellant is not; along with the inner container, the propellant is stored in the outer container. Similarly the pouch-type container of this invention consists of an outer container and a this invention consists of an outer container and a pouch having a valve. Only the skin care composition is contained in the pouch and the propellant is not; along with the pouch, the propellant is stored in teh outer container. Employment of such a method prevents the contact between the skin care composition and the propellant, thereby making it possible to prevent decomposition or degradation of the retinoid in the skin care composition.

A method of filling the contents in the inner container is not particularly limited and methods such that the oxygen does not invade the inner container and not contact the contents may be applicable, as known to those of ordinary skill in the art. Preferably, the contact between oxygen and the skin care composition of this invention should be performed such that filling takes place in an atmosphere of inert gas such as nitrogen or argon. The content is filled in the pouch as follows. First, the pouch and propellant are placed within the outer container and said outer container is then sealed with the valve. In this state, a gas within the pouch is expelled with the pressure of the propellant so that the inside of the pouch is almost completely degassed. After that, the content is filled in the pouch under pressure. The content is, when filled by this method, scarcely contacted with oxygen in the filling. Preferably, if the content is filled in inert gas such as nitrogen or argon, the contact with oxygen is more completely blocked.

Further, even after the content is filled, it is double partitioned from the open air by an oxygen-impermeable film used in the pouch and the outer container, and the contact between oxygen in an ambient atmosphere and the skin care composition within the pouch is completely prevented.

The conventional tube-type container is completely sealed before first opened. However, once it is opened and started to be used, entrance of oxygen is permitted whenever it is opened for use, though the contact with air is prevented with a cap during storage. Meanwhile, when the two-part container is used, oxygen does not enter even after starting to use it.

The material of the container of this invention in which the composition is out of contact with oxygen is not particularly limited. However, a multilayered film constituting the inner container in the two-compartment container is preferable, from the aspects of sealing retention, oxygen-barrier properties and stability to the skin care composition. More preferable is a multilayered film composed of at least two kinds selected from the group consisting of polyethylene terephthalate, nylon, aluminum, polypropylene, an AAS resin and an ethylene/vinyl alcohol copolymer. Especially preferable are a multilayered film obtained by laminating polyethylene terephthalate, nylon, aluminum and the AAS resin in this order as film materials from the innermost layer to the outermost layer of the pouch, and a multilayered film obtained by laminating polyethylene terephthalate, nylon, aluminum and polypropylene in this order as materials from the innermost layer to the outermost layer.

Polyethylene terephthalate is a polyester resin having a chemical structure obtained by polycondensing terephthalic acid with ethylene glycol. Nylon includes various polyamide resins. The AAS resin is a resinous polymer formed by graft polymerizing acrylonitrile as a main component with copolymer components including an acrylate ester and butadiene, and can be obtained, for example, under a trade name "BAREX" from Mitsui Toatsu Chemicals, Inc.

The ethylene/vinyl alcohol copolymer is a resinous polymer produced by saponifying a random copolymer of ethylene and vinyl acetate, and be obtained, for example, under a trade name "EVAL" from Kurary Co., Ltd.

The two-part container of this invention can be used, as is apparent from the foregoing explanation, in not only the retinoid-containing skin care composition but also liquid substances of various forms, e.g., an emulsion, a suspension, an aqueous solution and an oil. Especially, it is suitable for storage of substances required to protect the content from an external environment such as air.

Figure 1A:
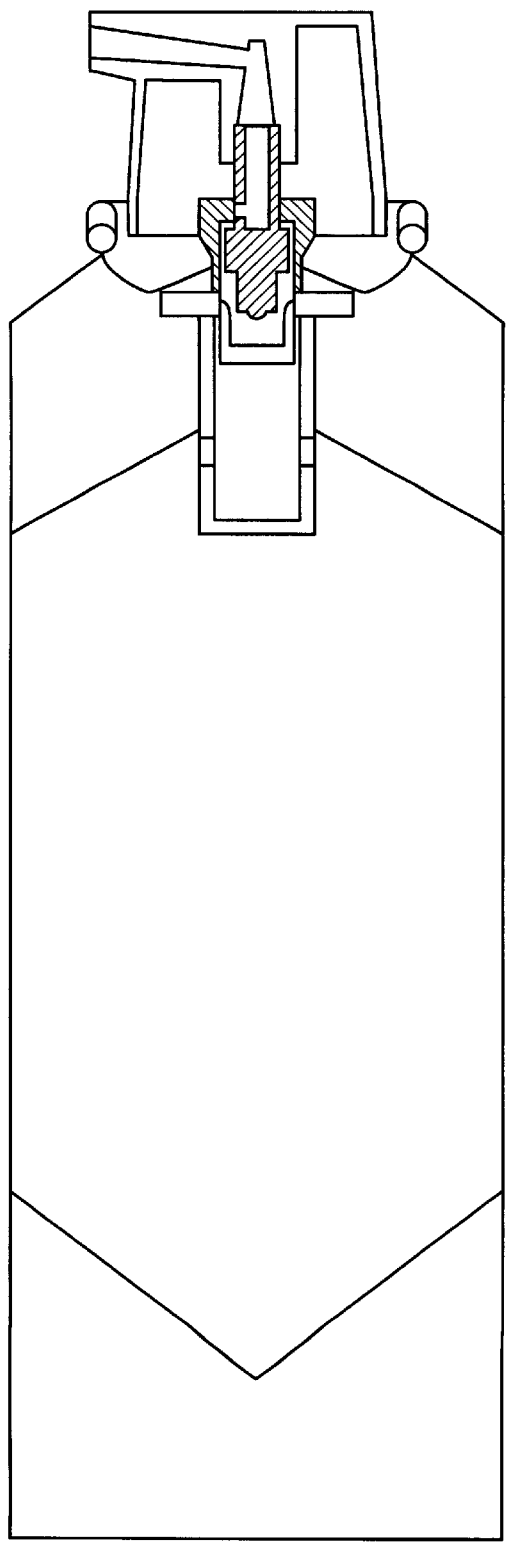
FIG. 1 is a front view of an example of an outer container in which the pouch of this invention is placed. When a cap is pushed down, a skin care composition is injected from an opening of a valve.
Figure 1B:
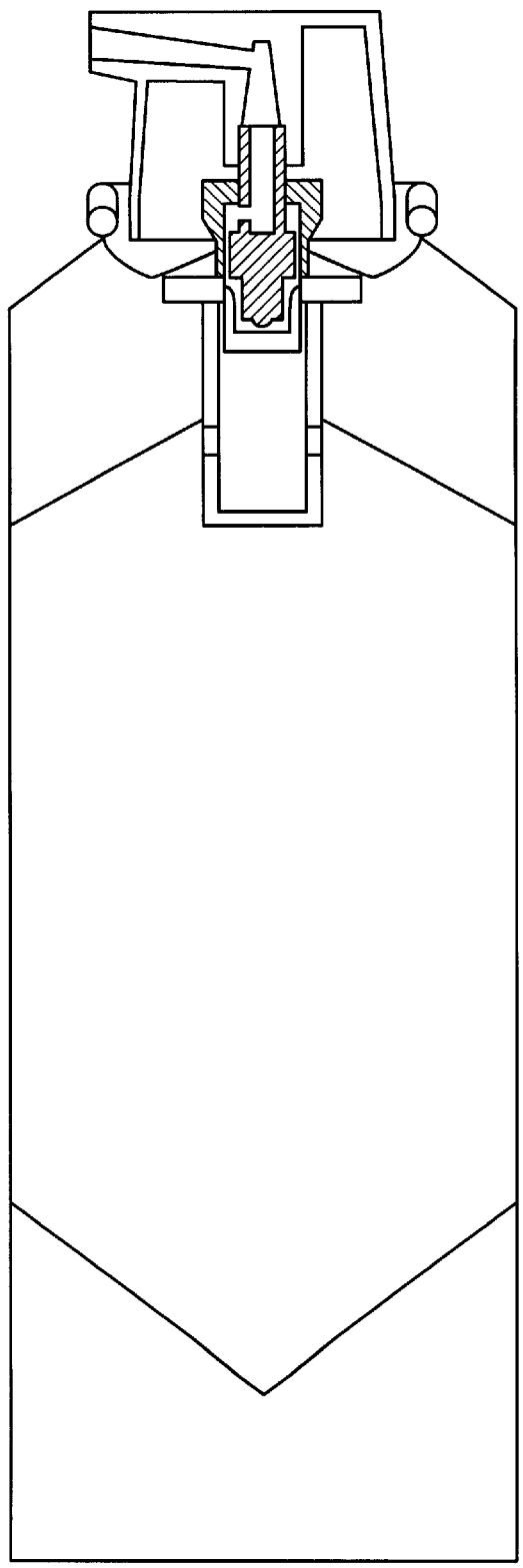
Figure 2:
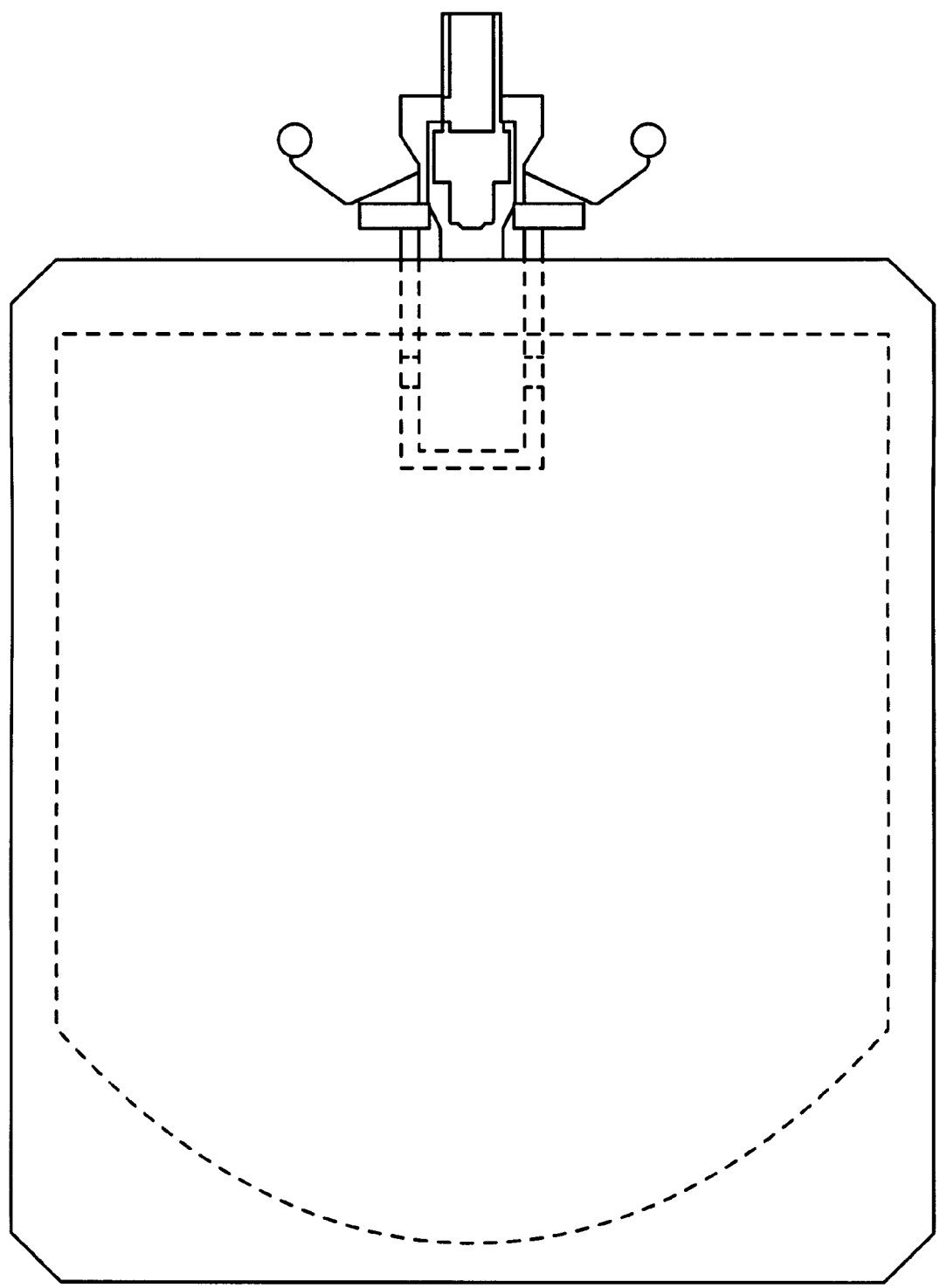
FIG. 2 is a front view of the pouch in this invention.
Figure 3:
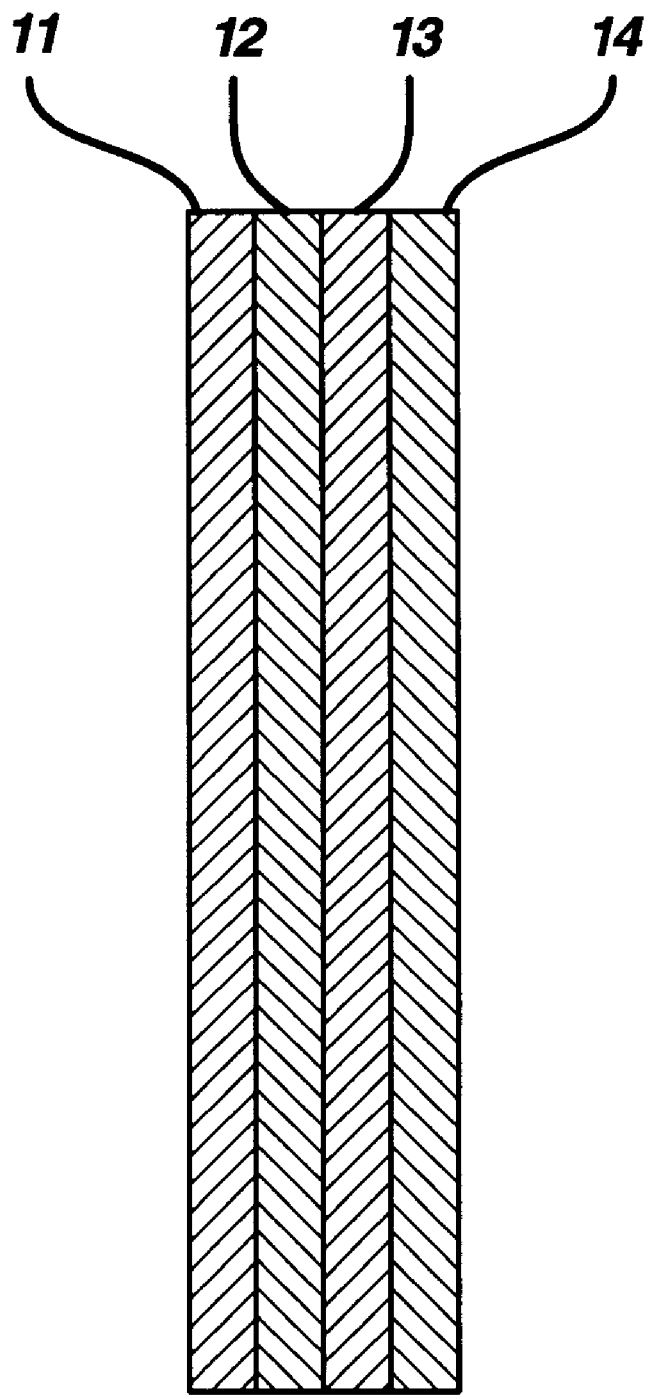
FIG. 3 is a sectional view of a multilayered film used in the pouch.

The advantages of the invention and specific embodiments of the skin care compositions prepared in accordance with the present invention are illustrated by the following examples. It will be understood, however, that the invention is not confined to the specific limitations set forth in the individual examples, but rather to the scope of the appended claims.

EXAMPLE 1

The formulations of this example 1 were prepared by first creating the water phase and then creating the oil phase. After both phases were created, they were mixed together and retinol added. The water phase was made by first weighing deionized water into a beaker and, with mixing at high speed, slowly adding carboxy polymer. The mixture was then stirred for a few minutes. EDTA and ascorbic acid were added to the mixture and mixing was continued for forty-five minutes or until well-dissolved. The water phase was then heated to 80 C, at which time propylene glycol was added. To make the oil phase, all ingredients of the oil phase were weighed and added together in a separate beaker. The oil phase was then heated to 80 C with mixing until homogeneous. The oil phase was then slowly phased into the water phase with mixing. After phasing, the emulsion was apportioned into four parts and sodium hydroxide was added at 80° C. to each portion separately in order to adjust the pH of the emulsion. The portions were adjusted to have pH of 4.5, 6.0, 7.0 and 9.0, respectively. After mixing for ten minutes, the emulsion was cooled to 45° C. Retinol 40% was then added to the emulsions and the emulsions mixed until homogeneous. The procedure was carried out under yellow light and under an argon blanket so as to minimize exposure to oxygen. Retinol concentrations were measured in accordance with the general HPLC procedure set forth below in Example 2, however, a different column was used containing a mobile of 65% acetonitrile, 35% phosphate buffer and a C18 column and a UV detector at 325 nm.

The components of the formulations of this example were as follows:

| Components | Content (% W/W) |
| --- | --- |
| Carboxyvinyl polymer | 0.300 |
| Propylene glycol | 5.00 |
| Methylparaben | 0.15 |
| Ascorbic Acid | 0.10 |
| Glyceryl monostearate | 5.00 |
| Cetanol | 1.00 |
| Stearyl alcohol | 0.50 |
| White Petrolatum | 1.50 |
| BHT | 0.05 |
| Propylparaben | 0.10 |
| Butylparaben | 0.05 |
| Cetyl palmitate | 1.00 |

-continued

| Components | Content (% W/W) |
| --- | --- |
| C12–C15 Alkyl Benzoate | 4.00 |
| Benzyl alcohol | 0.30 |
| Ethyl alcohol | 4.00 |
| Disodium EDTA | 0.05 |
| Retinol 40% | 0.366 |
| Sodium Hydroxide (10%) | to adjust pH |
| Water | q.s. |

The four emulsions were again apportioned into two parts each, and one of each part held at 50° C., the other part held at 40° C. The stability of all four emulsions was measured over a period of eight weeks. The stability data is set forth below in Table 1.

TABLE 1

| Weeks | Temperature | pH | % Retinol From Initial |
| --- | --- | --- | --- |
| 2 | 50° C. | 4.5 | 80.19 |
|  |  | 6.0 | 93.67 |
|  |  | 7.0 | 97.07 |
|  |  | 9.0 | 96.01 |
| 4 | 40° C. | 4.5 | 82.65 |
|  |  | 6.0 | 95.72 |
|  |  | 7.0 | 97.64 |
|  |  | 9.0 | 95.77 |
|  | 50° C. | 4.5 | 64.35 |
|  |  | 6.0 | 94.43 |
|  |  | 7.0 | 95.92 |
|  |  | 9.0 | 94.74 |
| 8 | 40° C. | 4.5 | 74.98 |
|  |  | 6.0 | 94.48 |
|  |  | 7.0 | 96.24 |
|  |  | 9.0 | 94.76 |
|  | 50° C. | 4.5 | 45.13 |
|  |  | 6.0 | 90.99 |
|  |  | 7.0 | 94.33 |
|  |  | 9.0 | 89.68 |

Thus, it can be seen that, although acceptable stabilities can be achieved at pH about 4.5, higher pH yields increased stability in the formulations of this invention.

EXAMPLE 1A

An oil-in-water emulsion was prepared in accordance with the procedure set forth in Example 1, using the components set forth below. Again, the emulsion was divided into four parts and the pH adjusted, this time to 4.5, 6.0, 8.0 and 10.0. Each part was further divided into two portions, one being held at 40° C. and one held at 50° C. for a period of seven weeks.

The results of the stability measurement are set forth in Table 1A below. Again, it can be seen that, as the pH increased, the stability increased.

| Components | Content (% W/W) |
| --- | --- |
| Disodium EDTA | 0.10 |
| Ascorbic Acid | 0.10 |
| Methylparaben | 0.15 |
| Mineral Oil | 8.00 |
| Stearyl Alcohol | 1.00 |
| BRIJ 721 (Steareth 21) | 2.00 |

-continued

| Components | Content (% W/W) |
|---|---|
| BRIJ 72 (Steareth-2) | 2.00 |
| BHT | 0.05 |
| Propylparaben | 0.10 |
| Retinol 40% | 0.366 |
| Deionized Water | Q.S. |
| Sodium Hydroxide 10% | to adjust pH |

TABLE 1A

| Weeks | Temperature | pH | % Retinol From Initial |
|---|---|---|---|
| 2 | 50° C. | 4.5 | 87.87 |
|  |  | 6.0 | 95.63 |
|  |  | 8.0 | 98.37 |
|  |  | 10.0 | 96.95 |
| 7 | 40° C. | 4.5 | 89.4 |
|  |  | 6.0 | 94.0 |
|  |  | 8.0 | 95.4 |
|  |  | 10.0 | 96.3 |
|  | 50° C. | 4.5 | 75.0 |
|  |  | 6.0 | 89.2 |
|  |  | 8.0 | 91.5 |
|  |  | 10.0 | 94.5 |

EXAMPLE 2

As a skin care composition containing a retinoid, an oil-in-water type lotion having the formulation shown in Table 2 was prepared in accordance with the procedure set forth in Example 1. As the retinoid, retinol was used. Concentrations of retinol and other retinoids such as retinal (vitamin A aldehyde), retinyl acetate and retinyl palmitate can be determined by any suitable analytical procedure. As reported herein, we determined retinoid concentrations by a high performance liquid chromatography (HPLC) procedure in which the chromatograph was equipped with a reversed phase 5 micron C-8 column (25 cm in length×4.6 mm in diameter) and a UV detector at 340 nm. The sample to be analyzed was diluted with a solution of 50% by weight methanol and 50% by weight ethyl acetate to a concentration of 18 micrograms/ml and the retinoid was detected at 340 nm. The gradient mobile phase consisted of an organic portion composed of 5 percent tetrahydrofuran in acetonitrile and an aqueous portion consisting of 0.05N ammonium acetate. The solvent program has an initial composition of 70% organic/30% aqueous which increases linearly to 80% organic /20% aqueous at 3 minutes, then again increases linearly to 100% organic at 15 minutes, where it stays until 19 minutes. After injecting 15 microliters of sample solution into the chromatograph, the analytical conditions were run at a flow rate of 2 ml/min and thermostatically regulated at 40° C. The retention time of retinol (Vitamin A alcohol) is about 6.4 minutes. The retention times of retinal (vitamin A aldehyde), retinyl acetate, and retinyl palmitate are about 7.5 mins., 10.1 mins. and 18.7 mins., respectively. The HPLC results were found to be reproducible to better than a 3% range of standard deviation.

TABLE 2

| Components | Content (% by Weight) |
|---|---|
| Carboxyvinyl polymer | 0.1 |
| Propylene glycol | 5.0 |
| Methylparaben | 0.15 |
| Sodium hydroxide | 0.041 |
| Ascorbic acid | 0.1 |
| Glyceryl monostearate | 5.0 |
| Cetanol | 1.0 |
| Stearyl alcohol | 0.5 |
| White Petrolatum | 1.5 |
| BHT | 0.05 |
| Propylparaben | 0.1 |
| Butylparaben | 0.05 |
| Cetyl palmitate | 1.0 |
| Higher alcohol benzoic acid ester | 4.0 |
| Benzyl alcohol | 0.3 |
| Ethyl alcohol | 5.0 |
| Disodium edetate | 0.05 |
| Retinol | 0.075 |
| Purified water | q.s. |
| Total | 100 |

A storage test was performed using three pouch-type aerosol containers of this invention which consisted of a pouch and contained LPG as a propellant correspondingly to the three test temperatures shown in Table 3. The pouch of said aerosol container was produced with a four-layered film obtained by laminating polyethylene terephthalate, nylon, aluminum and an AAS resin in this order as film materials from the innermost layer to the outermost layer. The above skin care composition was distributed in each of the three containers to form three samples. The method of distribution of the skin care composition is as follows. First, the pouch is placed in the outer container and LPG is charged in the outer container and outside of the pouch and sealed, thereby a gas in the pouch is expelled with the pressure of the LPG. In this state, the skin care composition is filled in the pouch under pressure. The three samples were allowed to stand in a constant temperature chamber adjusted to 40° C.±1° C., a constant temperature chamber adjusted to 4° C.±1° C. and at room temperature. Samples for analysis were collected from the same samples through an injection nozzle with the pressure of the propellant before the start of the test, 4 weeks later, 8 weeks later and 13 weeks later. One gram of each sample for analysis was accurately weighed and collected. A retinoid was extracted with an ethyl acetate/methanol mixed solution, and an amount of the retinoid was determined by a light absorption analysis at a wave length of 325 nm using a liquid chromatograph. The results are shown in Table 3 below.

EXAMPLE 3

The storage test was performed to determine the amount of a retinoid in the same manner as in Example 2 except that a pouch was used which was produced with a four-layered film obtained by laminating polyethylene terephthalate, nylon, aluminum and polypropylene in this order as materials form the innermost layer to the outermost layer, that a nitrogen gas was used as a propellant and that the distribution of the skin care composition is performed by the following method, a pouch is placed in an outer container then the skin care composition is filled in the pouch, the pouch is sealed with a valve, a nitrogen gas is charged inside the outer container and outside the pouch and sealed. The results are shown in Table 3.

COMPARATIVE EXAMPLES 1 AND 2

The storage test was performed to determine the amount of a retinoid in the same manner as in Example 1 at the temperature listed in Table 2 below, except using a sealed aluminum tube-in Comparative Example 1, an aerosol container not using a pouch in Comparative Example 2. The results are shown in Table 2. When an aluminum tube was used, nine sealed samples were prepared. Under the respective temperature conditions, the unopened sealed samples were opened 4 weeks later, 8 weeks later and 13 weeks later, and samples for analysis were then collected.

TABLE 3

| Example No. | Temperature | 4 weeks later | 8 weeks later | 13 weeks later |
|---|---|---|---|---|
| Example 1 | 40° C. | 90.7 | 88.9 | 93.2 |
|  | room temp. | 93.4 | 90.3 | 92.0 |
|  | 4° C. | 95.1 | 93.0 | 94.9 |
| Example 2 | 40° C. | 89.0 | 87.0 | 86.2 |
|  | room temp. | 92.0 | 87.9 | 88.6 |
|  | 4° C. | 93.2 | 91.2 | 91.6 |
| Comparative Example 1 | 40° C. | 83.5 | 80.9 | 80.7 |
|  | room temp. | 86.6 | 88.0 | 82.1 |
|  | 4° C. | 89.5 | 86.8 | 88.7 |
| Comparative Example 2 | 40° C. | 85.0 | 85.3 | 81.4 |
|  | room temp. | 89.3 | 86.5 | 86.9 |

EXAMPLE 4

An oil-in-water type lotion having a formulation shown in Table 4 was prepared. The lotion was filled in the pouch-type aerosol container and the storage test for four weeks and eight weeks was performed as in Example 2 except that a nitrogen gas was used as a propellant.

TABLE 4

| Components | Content (% by weight) |
|---|---|
| Carboxyvinyl polymer | 0.25 |
| Propylene glycol | 5.0 |
| Methylparaben | 0.15 |
| Sodium hydroxide | 0.041 |
| Ascorbic acid | 0.1 |
| Glyceryl monostearate | 5.0 |
| Cetanol | 1.0 |
| Stearyl alcohol | 0.5 |
| White Petrolatum | 1.5 |
| BHT | 0.05 |
| Propylparaben | 0.1 |
| Butylparaben | 0.05 |
| Cetyl palmitate | 1.0 |
| Higher alcohol benzoic acid ester | 4.0 |
| Benzyl alcohol | 0.3 |
| Ethyl alcohol | 5.0 |
| Disodium edetate | 0.05 |
| Retinol | 0.075 |
| Purified water | q.s. |
| Total | 100 |

COMPARATIVE EXAMPLE 3

The lotion prepared in Example 3 was filled in a jar container and the storage test for four weeks and eight weeks was performed as in Example 3. The results of Example 3 and Comparative Example 3 are shown in Table 5.

TABLE 5

| Example No. | Temperature | 4 weeks later | 8 weeks later |
|---|---|---|---|
| Example 3 | 40° C. | 95.7 | 94.9 |
|  | room temp. | 96.4 | 96.0 |
|  | 4° C. | 97.0 | 99.9 |
| Comparative Example 3 | 40° C. | 70.0 | 62.8 |
|  | room temp. | 94.6 | 90.3 |
|  | 4° C. | 96.1 | 98.9 |

EXAMPLE 4

An oil-in-water type lotion having the formulation shown in Table 6 was prepared.

TABLE 6

| Components | Content (% by weight) |
|---|---|
| Carboxyvinyl polymer | 0.3 |
| Propylene glycol | 5.0 |
| Methylparaben | 0.15 |
| Sodium hydroxide | 0.041 |
| Ascorbic acid | 0.1 |
| Glyceryl monostearate | 5.0 |
| Cetanol | 1.0 |
| Stearyl alcohol | 0.5 |
| White Petrolatum | 1.5 |
| BHT | 0.05 |
| Propylparaben | 0.1 |
| Butylparaben | 0.05 |
| Cetyl palmitate | 1.0 |
| Higher alcohol benzoic acid ester | 4.0 |
| Benzyl alcohol | 0.3 |
| Ethyl alcohol | 5.0 |
| Disodium edetate | 0.05 |
| Retinol | 0.075 |
| Purified water | q.s. |
| Total | 100 |

The storage test was performed in the same manner as in Example 1 except that a two-compartment container whose propellant is LPG was used and that the distribution of the skin care composition is performed in an atmosphere of an inert gas. The results are shown in Table 7.

COMPARATIVE EXAMPLE 4

The lotion prepared in Example 4 was filled in a jar container and the storage test was performed as in Example 4. The results of Comparative Example 4 are shown in Table 7.

TABLE 7

| Example No. | Temperature | 4 weeks later | 8 weeks later | 13 weeks later |
|---|---|---|---|---|
| Example 4 | 40° C. | 92.6 | 89.2 | 87.4 |
|  | room temp. | 93.4 | 90.7 | 91.0 |
|  | 4° C. | 98.1 | 95.2 | 93.5 |
| Comparative Example 4 | 40° C. | 81.1 | 77.6 | 52.5 |
|  | room temp. | 91.0 | 82.6 | 84.8 |
|  | 4° C. | 92.4 | 91.7 | 92.7 |

EXAMPLE 5

A formulation was prepared in accordance with the procedure set forth in Example 1, except that the following components were used.

| Components | Content (% by weight) | |
|---|---|---|
| | Formula A | Formula B |
| Deionized Water | Q.S | Q.S |
| Sorbitol | 5.0 | 5.00 |
| Methylparaben | 0.15 | 0.15 |
| Disodium EDTA | 0.02 | 0.02 |
| Span 60 | 3.00 | 3.00 |
| Tween 60 | 4.00 | 4.00 |
| Beeswax | 0.95 | 0.95 |
| Safflower oil | 3.33 | 0.00 |
| Liquid Paraffin | 4.94 | 8.27 |
| BHT | 0.03 | 0.03 |
| Propylparaben | 0.10 | 0.10 |
| Fragrance | 0.15 | 0.15 |
| Retinol 40% | 0.37 | 0.37 |

The formulations A and B were divided into two. One portion each of formulation A and B was held at 40° C.; one portion each of formulation A and B was held at 50° C. for one week. After one week, stability of the retinol was measured. The results are set forth in Table 8 below. It can be seen that, after one week, formulation A, which contains safflower oil, an unsaturated oil, has significantly less retinol than that of formulation B, which does not contain unsaturated safflower oil.

TABLE 8

| Weeks | Temperature | % Retinol From Initial | |
|---|---|---|---|
| | | Formula A | Formula B |
| 1 | 40° C. | 89.0 | 92.0 |
| | 50° C. | 84.0 | 91.5 |

EXAMPLE 6

The formulations of this example 6 were prepared by the procedure set forth in Example 1.

| Component | 6-I | 6-II | 6-III | 6-IV | 6-V |
|---|---|---|---|---|---|
| Vitamin A Alcohol | 0.166 | 0.166 | 0.166 | 0.166 | 0.166 |
| Carbomer | 0.30 | 0.30 | 0.30 | 0.30 | 0.30 |
| Propylene Glycol | 5.00 | 5.00 | 5.00 | 5.00 | 5.00 |
| Methyl Paraben | 0.15 | 0.15 | 0.15 | 0.15 | 0.15 |
| Sodium Hydroxide 10% solution | 1.00 | 1.00 | 1.00 | 1.00 | 1.00 |
| Ascorbic Acid | — | — | — | — | 0.10 |
| Glyceryl Stearate & PEG-100 Stearate | 5.00 | 5.00 | 5.00 | 5.00 | 5.00 |
| Cetyl Alcohol | 1.00 | 1.00 | 1.00 | 1.00 | 1.00 |
| Stearyl Alcohol | 0.50 | 0.50 | 0.50 | 0.50 | 0.50 |
| White Petrolatum | 1.50 | 1.50 | 1.50 | 1.50 | 1.50 |
| Butylated Hydroxytoluene | — | — | 0.05 | 0.05 | 0.05 |
| Propyl Paraben | 0.10 | 0.10 | 0.10 | 0.10 | 0.10 |
| Butyl Paraben | 0.05 | 0.05 | 0.05 | 0.05 | 0.05 |
| C12–15 Alcohols Benzoate | 4.00 | 4.00 | 4.00 | 4.00 | 4.00 |
| Cetyl Palmitate | 1.00 | 1.00 | 1.00 | 1.00 | 1.00 |
| Benzyl Alcohol | 0.30 | 0.30 | 0.30 | 0.30 | 0.30 |
| SD Alcohol 40-B | 5.00 | 5.00 | 5.00 | 5.00 | 5.00 |
| Disodium EDTA | — | 0.05 | — | 0.05 | 0.05 |
| Deionized Water | q.s. | q.s. | q.s. | q.s. | q.s. |

The stability of the formulations was measured by determining the amount of all-trans retinol after storage for various time periods at 40° C.

Figure 4:
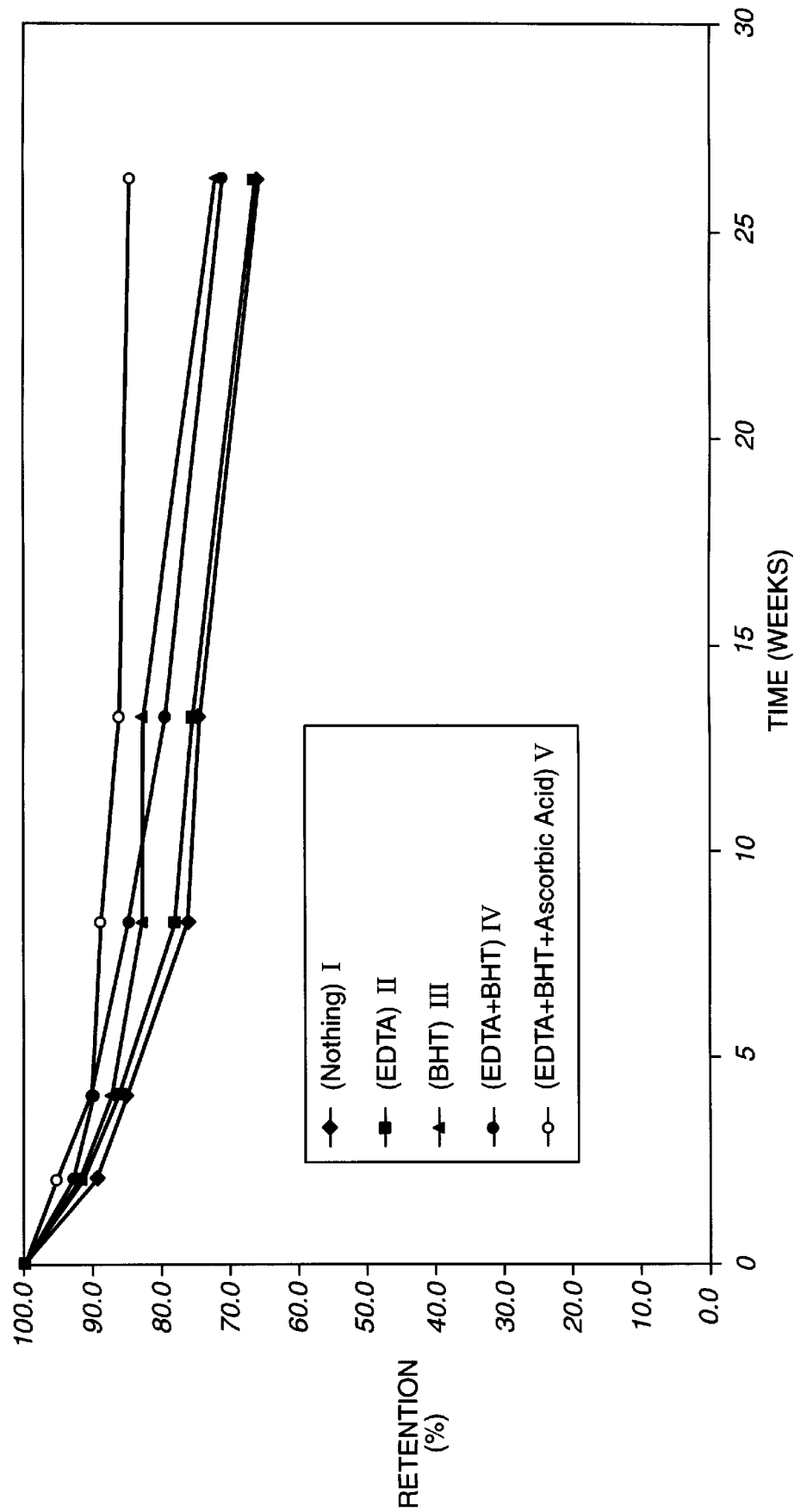

The results of this Example 6 are set forth in the graph in FIG. 4 hereto. After 13 weeks of aging, all the Formulations I–V retained at least 70% of the initial all-trans retinol in the compositions. The addition of a chelator, EDTA in Formulation 6-II improved the stability to a small extent. The addition of BHT, an oil-soluble anti-oxidant, in Formulation 6-III resulted in a relatively large improvement in stability. The use of both EDTA and BHT in Formulation 6-IV also resulted in another improvement. The use of a chelator, an oil-soluble anti-oxidant and ascorbic acid, a water-soluble anti-oxidant, in Formulation 6-V, resulted in an excellent stability, retaining approximately 90% of the initial all-trans retinol not only at 13 weeks, but at 25 weeks as well.

EXAMPLE 7

Another formulation in accordance with this invention contains the following ingredients:

| Ingredient | % W/W |
|---|---|
| Deionized Water | 83.38 |
| Carbomer | 0.35 |
| Methylparaben | 0.20 |
| Disodium EDTA | 0.10 |
| D-Panthenol | 0.50 |
| Glycerin | 3.00 |
| C12–15 Alkyl Benzoate | 4.00 |
| Octyl Hydroxystearate | 1.00 |
| Dimethicone 100 cs | 1.00 |
| Cetyl Alcohol | 2.50 |
| Ceteryl Glucoside | 1.40 |
| BHT | 0.10 |
| Tocopherol Acetate | 0.50 |
| Propylparaben | 0.10 |
| Triethanolamine 99% | 0.40 |
| Tocopherol | 0.05 |
| Retinol 40% | 0.118 |
| Japanese Tea Extract | 1.00 |
| Diazolidinyl Urea | 0.30 |

The formulation of this Example 7 was found to be quite stable and is an acceptable emulsion for use on the face and other skin.

EXAMPLE 8

Another formulation in accordance with this invention contains the following ingredients:

EXAMPLE 8-I

| Ingredient | % W/W |
|---|---|
| Deionized Water | q.s. |
| Carbomer | 0.35 |
| Methylparaben | 0 20 |
| Disodium EDTA | 0.10 |
| D-Panthenol | 0.50 |
| Glycerin | 3.00 |
| C12–15 Alkyl Benzoate | 4.00 |
| Octyl Hydroxystearate | 1.00 |
| Dimethicone 100 cs | 1.00 |
| Cetyl Alcohol | 2.50 |
| Ceteryl Glucoside | 1.40 |
| BHT | 0.10 |
| Tocopherol Acetate | 0.50 |
| Propylparaben | 0.10 |
| Deionized Water | 1.50 |
| Triethanolamine 99% | 0.40 |
| Tocopherol | 0.05 |

-continued

| Ingredient | % W/W |
|---|---|
| Retinol 40% | 0.3825 |
| Japanese Tea Extract | 1.00 |
| Deionized Water | 2.00 |
| Diazolidinyl Urea | 0.30 |

The formulation of this Example 8-I is quite stable and is an acceptable emulsion for use on the face and other skin. After thirteen weeks of storage at 40 C, 97% of the initial level of all-trans retinol was present in the composition of this example.

Another formulation was prepared in accordance with the procedure of this example, having the following formulation:

Example 8-II

| Ingredient | % W/W |
|---|---|
| Deionized Water | q.s. |
| Carbomer | 0.35 |
| Methylparaben | 0.20 |
| Disodium EDTA | 0.10 |
| D-Panthenol | 0.50 |
| Glycerin | 3.00 |
| C12–15 Alkyl Benzoate | 4.00 |
| Octyl Hydroxystearate | 2.00 |
| Cetyl Alcohol | 2.50 |
| Cetearyl Glucoside | 2.50 |
| BHT | 0.10 |
| Tocopherol Acetate | 0.50 |
| Propylparaben | 0.10 |
| Deionized Water | 1.50 |
| Triethanolamine 99% | 0.40 |
| Tocopherol | 0.05 |
| Retinol 40% | 0.3825 |
| Japanese Tea Extract | 1.00 |
| Deionized Water | 2.00 |
| Diazolidinyl Urea | 0.30 |

The formulation of this Example 8-II is quite stable and is an acceptable emulsion for use on the face and other skin. After thirteen weeks of storage at 40° C., 88% of the initial level of all-trans retinol was present in the composition of this example.

EXAMPLE 9A

A sunscreen-containing formulation was made in accordance with the procedure set forth in Example 1, containing retinol and an active inorganic sunscreen ingredient, titanium dioxide. The formulation of this example is as follows:

| Ingredient | % W/W |
|---|---|
| Deionized Water | q.s. |
| Glycerine | 3.00 |
| Sodium Chloride | 0.50 |
| Panthenol | 0.50 |
| Disodium EDTA | 0.20 |
| Allantoin | 0.15 |
| Sodium metabisulfite | 0.10 |
| Octyl Pelargonate | 9.00 |
| Titanium Dioxide | 6.00 |
| Cyclomethicone | 6.00 |
| Cetyl Dimethicone Copolyol | 3.60 |

-continued

| Ingredient | % W/W |
|---|---|
| Retinol 10% | 0.46 |
| Cetyl Dimethicone | 1.50 |
| Dimethicone | 1.00 |
| Bisabolol | 0.20 |
| Tocopheryl Acetate | 0.10 |
| Butylated Hydroxytoluene | 0.05 |
| Talc | 1.00 |
| Phenoxyethanol | 0.20 |
| Isopropylparaben, Isobutylparaben, N-Butylparaben | 0.80 |

EXAMPLE 9B

Another formulation was created containing an organic sunscreen and retinol. The organic sunscreen used was octyl methoxycinnamate. This formulation had sunblock activity as well as having the other attributes of retinoid-containing formulations. The formulation was

| Ingredient | % W/W |
|---|---|
| Deionized Water | 66.84 |
| Glycerine | 5.00 |
| Panthenol | 0.50 |
| Disodium EDTA | 0.20 |
| Allantoin | 0.15 |
| Carbomer | 0.30 |
| Sodium metabisulfite | 0.10 |
| Octyl Methoxycinnamate | 6.00 |
| Glyceryl Stearate & PEG-100 Stearate | 5.00 |
| C12–C15 Alkyl Benzoate | 4.00 |
| White Petrolatum | 1.50 |
| Lauroyl Lysine | 1.00 |
| Cetyl Alcohol | 1.00 |
| Cetyl Palmitate | 1.00 |
| Stearyl Alcohol | 0.50 |
| Retinol 10% | 0.46 |
| Butylated Hydroxytoluene | 0.05 |
| SD Alcohol 40-B | 5.00 |
| Sodium Hydroxide | 1.00 |
| Isopropylparaben, Isobutylparaben, N-Butylparaben | 0.40 |

EXAMPLE 10

In yet another formulation, a retinol-containing composition was made for topical use. The composition was made in accordance with Example 1 above. The ingredients were as follows:

| Ingredient | % W/W |
|---|---|
| Deionized Water | 72.84 |
| Glycerine | 5.00 |
| Panthenol | 0.50 |
| Disodium EDTA | 0.20 |
| Allantoin | 0.15 |
| Carbomer | 0.30 |
| Sodium metabisulfite | 0.10 |
| Glyceryl Stearate & PEG-100 Stearate | 5.00 |
| C12–C15 Alkyl Benzoate | 4.00 |
| White Petrolatum | 1.50 |
| Lauroyl Lysine | 1.00 |
| Cetyl Alcohol | 1.00 |
| Cetyl Palmitate | 1.00 |
| Stearyl Alcohol | 0.50 |
| Retinol 10% | 0.46 |
| Butylated Hydroxytoluene | 0.05 |

-continued

| Ingredient | % W/W |
|---|---|
| SD Alcohol 40-B | 5.00 |
| Sodium Hydroxide | 1.00 |
| Isopropylparaben, Isobutylparaben, N-Butylparaben | 0.40 |

EXAMPLE 11

Formulations in accordance with this invention may also be made containing azole-type compounds, such as itraconazole, miconazole and ketoconazole. The nitrate or other salt forms of the imidazoles should not be used, however, as they tend to render unstable the retinoids contained in the formulations. In this example, the following ingredients were combined to make imidazole-containing formulations according to the teachings of this invention.

| | % W/W | | |
|---|---|---|---|
| Ingredient | 11-I | 11-II | 11-III |
| Water Phase | | | |
| Deionized Water | q.s. 100% | q.s. 100% | q.s. 100% |
| Carbomer 940 | 0.22 | 0.22 | 0.22 |
| Disodium EDTA dihydrate | 0.10 | 0.10 | 0.10 |
| Propylene Glycol | 5.00 | 5.00 | 5.00 |
| Oil Phase | | | |
| Arlacel 165 | 5.0 | 5.0 | 5.0 |
| Cetyl Alcohol | 1.0 | 1.0 | 1.0 |
| Stearyl Alcohol | 0.5 | 0.5 | 0.5 |
| White Petrolatum | 1.5 | 1.5 | 1.5 |
| BHT | 0.05 | 0.05 | 0.05 |
| Methylparaben | 0.15 | 0.15 | 0.15 |
| Propylparaben | 0.1 | 0.1 | 0.1 |
| Butylparaben | 0.05 | 0.05 | 0.05 |
| C12–15 Alkyl benzoate | 4.0 | 4.0 | 4.0 |
| Cetyl Palmitate | 1.0 | 1.0 | 1.0 |
| Ketoconazole | 2.0 | — | — |
| Miconazole base | — | 2.0 | — |
| Miconazole nitrate | — | — | 2.0 |
| Ethyl Alcohol | 5.0 | 5.0 | 5.0 |
| Benzyl Alcohol | 0.3 | 0.3 | 0.3 |
| Retinol 40% | 0.332 | 0.332 | 0.332 |
| Sodium Hydroxide | | (adjust pH) | |

The formulations were made in accordance with the procedures set forth in Example 1, except that the imidazoles were added to the oil phase immediately before phasing the oil phase into the water phase. The stability of formulation 11-I at thirteen weeks of storage at 40° C. was such that 82% of the initial retinol was present. In formulation 11-II, after four weeks, 90% of the initial retinol remained compared with 71% of the initial retinol in formulation 11-III after four weeks. Thus, good stability was achieved in imidazole-containing formulations according to this invention.

EXAMPLE 12

In another formulation, the following composition was prepared as an oil-in-water emulsion:

| Ingredient | % W/W |
|---|---|
| Water Phase | |
| Deionized Water | 65.74 |
| Carbopol 934 (carboxyvinyl polymer) | 0.30 |
| Sodium EDTA | 0.05 |
| Sodium bisulfite | 0.10 |
| Butyl Paraben | 0.05 |
| Methyl Paraben | 0.15 |
| Propyl Paraben | 0.01 |
| Allantoin | 0.15 |
| Panthenol | 0.50 |
| Propylene Glycol | 5.00 |
| Oil Phase | |
| Arlacel 165 | 5.00 |
| Cetyl Alcohol | 1.00 |
| Stearyl Alcohol | 1.50 |
| White Petrolatum | 1.50 |
| Octyl Methoxycinnamate | 6.00 |
| BHT | 0.05 |
| C12–15 Alkyl Benzoates | 4.00 |
| Cetyl Palmitate | 1.00 |
| Retinol Phase | |
| Sodium Hydroxide @ 10% | 1.00 |
| Ethyl Alcohol | 5.00 |
| Benzyl Alcohol | 0.30 |
| Lauroyl lysine | 1.00 |
| Retinol 10% in Soy Bean Oil | 1.59 |

Deionized water was weighed into a suitable beaker. Nitrogen gas was bubbled through water, heat was applied and the water was mixed. At high speed mixing, Carbopol 934 was slowly added to deionized water, and mixed for five minutes. The Disodium EDTA and sodium bisulfite were added to this mixture. At 60° C., methyl, propyl, and butyl paraben were added, in addition to allantoin and panthenol and the mixing continued. At 80° C., propylene glycol was added and the composition mixed.

In a separate beaker, the oil phase ingredients were weighed one by one while heat was applied. The mixture was heated to 80° C. and mixed until homogeneous. The oil mixture was phased into the water phase slowly with mixing, and cooling was begun. At 60° C., the sodium hydroxide, lauroyl lysine and Retinol in soy bean oil were added. At about 35° C., ethyl alcohol and benzyl alcohol were added and mixing continued for about 10 minutes. Water was added q.s. and the formulation mixed for about five minutes until the batch was homogeneous.

The pH of the formulation of this example was about 6.6. The batch appeared creamy, glossy, smooth, homogeneous and off-white.

EXAMPLE 13

Retinaldehyde-containing compositions were made in accordance with the following procedure. Operating under yellow light and an argon gas blanket, deionized water was weighed out in a beaker. Carbopol was slowly added and the composition mixed well until dissolved. Disodium EDTA and methyl paraben were added to the mixture and the mixture was heated to 80° C. At 80° C., propylene glycol was added. The oil phase ingredients were weighed and placed into a separate beaker. The mixture was heated to 80° C. with stirring and dimethicone added. With both phases at 80° C., the oil phase was added to the water phase and mixed. In formulation 13-I, a 50% sodium hydroxide solution was added for pH adjustment. Prior to adding the retinaldehyde, the mixture was held at 80° C. for ten minutes, then cooled to 30° C. Retinaldehyde was mixed with benzyl alcohol and added to the mixture. In formulation 13-II, citral was added to the premixture containing benzyl alcohol and retinaldehyde.

| Ingredient | % W/W | |
|---|---|---|
| | 13-I | 13-II |
| Water Phase | | |
| Deionized Water | 82.29 | 82.29 |
| Carbomer 941 (carboxyvinyl polymer) | 0.30 | 0.30 |
| Propylene Glycol | 4.00 | 4.00 |
| Methylparaben | 0.30 | 0.30 |
| Disodium EDTA | 0.10 | 0.10 |
| Oil Phase | | |
| Myristyl Myristate | 1.50 | 1.50 |
| Glyceryl Stearate | 1.25 | 1.25 |
| stearic Acid | 1.25 | 1.25 |
| Oleic Acid | 1.25 | 1.25 |
| Polysorbate 61 | 1.20 | 1.20 |
| Isopropyl Palmitate | 1.00 | 1.00 |
| Stearoxytrimethylsilane | 1.00 | 1.00 |
| Dimethicone | 1.00 | 1.00 |
| Sorbitan Stearate | 0.80 | 0.80 |
| Synthetic Beeswax | 0.50 | 0.50 |
| Cetyl Alcohol | 0.50 | 0.50 |
| Stearyl Alcohol | 0.50 | 0.50 |
| BHT | 0.02 | 0.02 |
| Propylparaben | 0.10 | 0.10 |
| Butylparaben | 0.05 | 0.05 |
| Benzyl Alcohol | 0.30 | 0.30 |
| Sodium Hydroxide | 0.2 | 0.2 |
| Citral | — | 1.6 |
| Retinaldehyde | 0.05 | 0.05 |

Two other formulations containing retinaldehyde were made as follows. Deionized water was weighed into a beaker and with mixing at high speed, carbopol was added slowly. After a few minutes, EDTA was added, as well as ascorbic acid. Mixing was continued for about 45 minutes until the mixture was well dissolved. The mixture was heated to 80° C. and propylene glycol added. In a separate beaker all ingredients were placed. The beaker was heated to 80° C. with mixing until homogeneous. The oils were then slowly phased into the water phase with mixing. Sodium hydroxide was added at 80° C. and the emulsion mixed for about ten minutes. Cooling was begun. At 35° C., benzyl alcohol was added. The batch was q.s. to 997 gm weight with water. The emulsion was mixed until uniform, about five minutes. The batch was then split into two portions. To one batch was added ethanol and retinaldeyde which had been premixed and dissolved. To the second batch was added a premix of ethanol, citral and retinaldehyde. The batches were then filled into blind aluminum tubes and stored at 40° C. for thirteen weeks. The formulations were as follows:

| Ingredient | % W/W | |
|---|---|---|
| | 13-III | 13-IV |
| Water Phase | | |
| Deionized Water | 75.85 | 74.25 |
| Carbomer 934P | 0.30 | 0.30 |

-continued

| Ingredient | % W/W | |
|---|---|---|
| | 13-III | 13-IV |
| Disodium EDTA | 0.05 | 0.05 |
| Ascorbic Acid | 0.10 | 0.10 |
| Propylene Glycol | 5.00 | 5.00 |
| Oil Phase | | |
| Glyceryl Monostearate | 5.0 | 5.0 |
| Cetyl Alcohol | 1.0 | 1.0 |
| Stearyl Alcohol | 0.5 | 0.5 |
| White Petrolatum | 1.5 | 1.5 |
| BHT | 0.05 | 0.05 |
| Methylparaben | 0.15 | 0.15 |
| Propylparaben | 0.1 | 0.1 |
| Butylparaben | 0.05 | 0.05 |
| C12–15 Alkyl benzoate | 4.0 | 4.0 |
| Cetyl Palmitate | 1.0 | 1.0 |
| Sodium Hydroxide 10% | 1.0 | 1.0 |
| Ethyl Alcohol | 4.0 | 4.0 |
| Benzyl Alcohol | 0.3 | 0.3 |
| Retinaldehyde | 0.05 | 0.05 |
| Citral | — | 1.6 |

All four formulations of this example were stored for thirteen weeks at 40° C. and had the following stabilities:

| Stability | 13-I | 13-II | 13-III | 13-IV |
|---|---|---|---|---|
| Conditions 13 wk/40° C. | 65% | 53% | 65% | 69% |

It is believed that, although the instability of retinal is even greater than that of retinol, through use of the methods and formulations of this invention, the stability can be improved. For example, an increase in pH in these formulations will result in an improved stability. In examples 13-I and 13-II, the C-value should be reduced as well.

What is claimed is:

1. A skin care composition comprising an oil-in-water emulsion and a therapeutically effective amount of a retinoid selected from the group consisting of Vitamin A alcohol, Vitamin A aldehyde, retinyl acetate, retinyl palmitate and mixtures thereof, said composition having a pH of between about 4 and about 10; said composition further comprising an oil phase, said oil phase comprising one or more oils having a total unsaturation density, or C value, of about 1200 or less, wherein C is calculated as follows:

$$C = A \times B,$$

wherein A is the percentage of an oil or fat in said composition and B is the iodine value of said oil or fat; said composition further comprising a stabilized system selected from the group consisting of:
  a) a stabilizing effective amount of at least one oil-soluble antioxidant present in said oil-phase of said emulsion;
  b) a stabilizing effective amount of a chelating agent present in the water phase of said emulsion and at least one oil-soluble antioxidant present in said oil phase of said emulsion;
  c) a stabilizing effective amount of a chelating agent present in said water phase of said emulsion; and
  d) a stabilizing effective amount of a chelating agent and an antioxidant present in each of the oil and water phases of said emulsion;

wherein said composition comprises less than about 12% by weight of a volatile silicone and said water-soluble antioxidant is selected from the group consisting of ascorbic acid, sodium sulfite, sodium bisulfite, sodium thiosulfite, sodium formaldehyde sulfoxylate, isoascorbic acid, thioglycerol, thiosorbitol, thiourea, thioglycolic acid, cysteine hyrochloride, 1,4-diazobicyclo-(2, 2,2)-octane, and mixtures thereof; said composition retaining at least about 70% of said retinoids after 13 weeks' storage at 40° C.

2. A skin care composition according to claim 1 wherein the water-soluble antioxidant is ascorbic acid.

3. A skin care composition according to claim 1 where the chelating agent is selected from the group consisting of ethylenediamine tetra acetic acid (EDTA) and salts thereof.

4. A skin care composition according to claim 1 wherein said stabilizing system comprises an oil-soluble antioxidant.

5. A skin care composition comprising an oil-in-water emulsion and a therapeutically effective amount of a retinoid selected from the group consisting of Vitamin A alcohol, Vitamin A aldehyde, retinyl acetate, retinyl palmitate and mixtures thereof, said composition having a pH of between about 4 and about 10; said composition further comprising an oil phase, said oil phase comprising one or more oils having a total unsaturation density, or C value, of about 1200 or less, wherein C is calculated as follows:

$$C = A \times B,$$

wherein A is the percentage of an oil or fat in said composition and B is the iodine value of said oil or fat; said composition further comprising a stabilized system selected from the group consisting of:
 a) a stabilizing effective amount of at least one oil-soluble antioxidant present in said oil-phase of said emulsion;
 b) a stabilizing effective amount of a chelating agent present in the water phase of said emulsion and at least one oil-soluble antioxidant present in said oil phase of said emulsion;
 c) a stabilizing effective amount of a chelating agent present in said water phase of said emulsion; and
 d) a stabilizing effective amount of a chelating agent and an antioxidant present in each of the oil and water phases of said emulsion;
wherein said stabilizing system comprises a chelating agent, an oil-soluble antioxidant and a water-soluble antioxidant and wherein said composition comprises less than about 12% by weight of a volatile silicone and said chelating agent is selected from the group consisting of ethylenediamine tetra acetic acid (EDTA) and salts thereof, dihydroxyethyl glycine, citric acid, tartaric acid, and mixtures thereof; said composition retaining at least about 70% of said retinoids after 13 weeks' storage at 40° C.

6. A skin care composition according to claim 5 where the chelating agent is selected from the group consisting of ethylenediamine tetra acetic acid (EDTA) and salts thereof.

7. A skin care composition comprising an oil-in-water emulsion and a therapeutically effective amount of a retinoid selected from the group consisting of Vitamin A alcohol, Vitamin A aldehyde, retinyl acetate, retinyl palmitate and mixtures thereof, said composition having a pH of between about 4 and about 10; said composition further comprising an oil phase, said oil phase comprising one or more oils having a total unsaturation density, or C value, of about 1200 or less, wherein C is calculated as follows:

$$C = A \times B,$$

wherein A is the percentage of an oil or fat in said composition and B is the iodine value of said oil or fat; said composition further comprising a stabilized system selected from the group consisting of:
 a) a stabilizing effective amount of at least one oil-soluble antioxidant present in said oil-phase of said emulsion;
 b) a stabilizing effective amount of a chelating agent present in the water phase of said emulsion and at least one oil-soluble antioxidant present in said oil phase of said emulsion;
 c) a stabilizing effective amount of a chelating agent present in said water phase of said emulsion; and
 d) a stabilizing effective amount of a chelating agent and an antioxidant present in each of the oil and water phases of said emulsion;
wherein said composition comprises less than about 12% by weight of a volatile silicone and an azole compound; said composition retaining at least about 70% of said retinoids after 13 weeks' storage at 40° C.

8. A skin care composition comprising an oil-in-water emulsion and a therapeutically effective amount of a retinoid selected from the group consisting of Vitamin A alcohol, Vitamin A aldehyde, retinyl acetate, retinyl palmitate and mixtures thereof, said composition having a pH of between about 4 and about 10; said composition further comprising an oil phase, said oil phase comprising one or more oils having a total unsaturation density, or C value, of about 1200 or less, wherein C is calculated as follows:

$$C = A \times B,$$

wherein A is the percentage of an oil or fat in said composition and B is the iodine value of said oil or fat; said composition further comprising a stabilized system selected from the group consisting of:
 a) a stabilizing effective amount of at least one oil-soluble antioxidant present in said oil-phase of said emulsion;
 b) a stabilizing effective amount of a chelating agent present in the water phase of said emulsion and at least one oil-soluble antioxidant present in said oil phase of said emulsion;
 c) a stabilizing effective amount of a chelating agent present in said water phase of said emulsion; and
 d) a stabilizing effective amount of a chelating agent and an antioxidant present in each of the oil and water phases of said emulsion;
wherein said composition comprises less than about 12% by weight of a volatile silicone and said chelating agent is selected from the group consisting of ethylenediamine tetra acetic acid (EDTA) and salts thereof, dihydroxyethyl glycine, citric acid, tartaric acid, and mixtures thereof; said composition retaining at least about 70% of said retinoids after 13 weeks' storage at 40° C.

9. A skin care composition according to claim 8 wherein said imidazole compound is selected from the group consisting of itraconazole, ketoconazole or miconazole.

10. A skin care composition comprising an oil-in-water emulsion and a therapeutically effective amount of a retinoid selected from the group consisting of Vitamin A alcohol, Vitamin A aldehyde, retinyl acetate, retinyl palmitate and mixtures thereof, said composition having a pH of between about 4 and about 10; said composition further comprising an oil phase, said oil phase comprising one or more oils having a total unsaturation density, or C value, of about 1200 or less, wherein C is calculated as follows:

$$C = A \times B,$$

wherein A is the percentage of an oil or fat in said composition and B is the iodine value of said oil or fat; said composition further comprising a stabilized system selected from the group consisting of:

a) a stabilizing effective amount of at least one oil-soluble antioxidant present in said oil-phase of said emulsion;

b) a stabilizing effective amount of a chelating agent present in the water phase of said emulsion and at least one oil-soluble antioxidant present in said oil phase of said emulsion;

c) a stabilizing effective amount of a chelating agent present in said water phase of said emulsion; and d) a stabilizing effective amount of a chelating agent and an antioxidant present in each of the oil and water phases of said emulsion;

wherein said composition comprises less than about 12% by weight of a volatile silicone and a corticosteroid sid composition retaining at least about 70% of said retinoids after 13 weeks' storage at 40° C.

11. A skin care composition according to claim 10 wherein said corticosteroid is hydrocortisone.

12. A skin care composition comprising an oil-in-water emulsion and a therapeutically effective amount of a retinoid selected from the group consisting of Vitamin A alcohol, Vitamin A aldehyde, retinyl acetate, retinyl palmitate and mixtures thereof, said composition having a pH of between about 4 and about 10; said composition further comprising an oil phase, said oil phase comprising one or more oils having a total unsaturation density, or C value, of about 1200 or less, wherein C is calculated as follows:

$$C = A \times B,$$

wherein A is the percentage of an oil or fat in said composition and B is the iodine value of said oil or fat; said composition further comprising a stabilized system selected from the group consisting of:

a) a stabilizing effective amount of at least one oil-soluble antioxidant present in said oil-phase of said emulsion;

b) a stabilizing effective amount of a chelating agent present in the water phase of said emulsion and at least one oil-soluble antioxidant present in said oil phase of said emulsion;

c) a stabilizing effective amount of a chelating agent present in said water phase of said emulsion; and d) a stabilizing effective amount of a chelating agent and an antioxidant present in each of the oil and water phases of said emulsion;

wherein said composition comprises less than about 12% by weight of a volatile silicone and a depigmentation agent; said composition retaining at least about 70% of said retinoids after 13 weeks' storage at 40° C.

13. A skin care composition according to claim 12 wherein said depigmentation agent is selected from the group consisting of licorice extract, hydroquinone, kojic acid, gatuline A, micromerol and mixtures thereof.

14. A skin care composition comprising an oil-in-water emulsion and a therapeutically effective amount of a retinoid selected from the group consisting of Vitamin A alcohol, Vitamin A aldehyde, retinyl acetate, retinyl palmitate and mixtures thereof, said composition having a pH of between about 4 and about 10; said composition further comprising an oil phase, said oil phase comprising one or more oils having a total unsaturation density, or C value, of about 1200 or less, wherein C is calculated as follows:

$$C = A \times B,$$

wherein A is the percentage of an oil or fat in said composition and B is the iodine value of said oil or fat; said composition further comprising a stabilized system selected from the group consisting of:

a) a stabilizing effective amount of at least one oil-soluble antioxidant present in said oil-phase of said emulsion;

b) a stabilizing effective amount of a chelating agent present in the water phase of said emulsion and at least one oil-soluble antioxidant present in said oil phase of said emulsion:

c) a stabilizing effective amount of a chelating agent present in said water phase of said emulsion; and d) a stabilizing effective amount of a chelating agent and an antioxidant present in each of the oil and water phases of said emulsion;

wherein said composition comprises less than about 12% by weight of a volatile silicone and a sunscreen agent; said composition retaining at least about 70% of said retinoids after 13 weeks' storage at 40° C.

15. A skin care composition according to claim 14 wherein said sunscreen agent is methoxycinnamate.

16. A skin care composition according to claim 14 wherein said sunscreen agent is selected from the group consisting of zinc oxide, titanium dioxide and mixtures thereof.

17. A skin care composition comprising an oil-in-water emulsion and a therapeutically effective amount of a retinoid selected from the group consisting of Vitamin A alcohol, Vitamin A aldehyde, retinyl acetate, retinyl palmitate and mixtures thereof, said composition having a pH of between about 4 and about 10; said composition further comprising an oil phase, said oil phase comprising one or more oils having a total unsaturation density, or C value, of about 1200 or less, wherein C is calculated as follows:

$$C = A \times B,$$

wherein A is the percentage of an oil or fat in said composition and B is the iodine value of said oil or fat; said composition further comprising a stabilized system selected from the group consisting of:

a) a stabilizing effective amount of at least one oil-soluble antioxidant present in said oil-phase of said emulsion;

b) a stabilizing effective amount of a chelating agent present in the water phase of said emulsion and at least one oil-soluble antioxidant present in said oil phase of said emulsion;

c) a stabilizing effective amount of a chelating agent present in said water phase of said emulsion; and d) a stabilizing effective amount of a chelating agent and an antioxidant present in each of the oil and water phases of said emulsion;

wherein said composition comprises less than about 12% by weight of a volatile silicone and an antioxidant; said composition retaining at least about 70% of said retinoids after 13 weeks' storage at 40° C.

18. A skin care composition according to claim 17 wherein said anti-oxidant is selected from the group consisting of ascorbic acid, vitamin B, biotin, pantothenic acid, vitamin D, vitamin E, vitamin C and sodium bisulfite.

19. A skin care composition comprising an oil-in-water emulsion and a therapeutically effective amount of a retinoid selected from the group consisting of Vitamin A alcohol, Vitamin A aldehyde, retinyl acetate, retinyl palmitate and mixtures thereof, said composition having a pH of between about 4 and about 10; said composition further comprising an oil phase, said oil phase comprising one or more oils having a total unsaturation density, or C value, of 500 or less, wherein C is calculated as follows:

$$C = A \times B,$$

wherein A is the percentage of an oil or fat in said composition and B is the iodine value of said oil or fat; said composition further comprising a stabilized system selected from the group consisting of:

a) a stabilizing effective amount of at least one oil-soluble antioxidant present in said oil-phase of said emulsion;

b) a stabilizing effective amount of a chelating agent present in the water phase of said emulsion and at least one oil-soluble antioxidant present in said oil phase of said emulsion;

c) a stabilizing effective amount of a chelating agent present in said water phase of said emulsion; and d) a stabilizing effective amount of a chelating agent and an antioxidant present in each of the oil and water phases of said emulsion;

wherein said composition comprises less than bout 12% by weight of a volatile silicone; said composition retaining at least about 70% of said retinoids after 13 weeks' storage at 40° C.

* * * * *